(12) United States Patent
Sperling et al.

(10) Patent No.: US 7,525,648 B2
(45) Date of Patent: Apr. 28, 2009

(54) APPARATUS FOR THE EXAMINATION OF THE PROPERTIES OF OPTICAL SURFACES

(75) Inventors: Uwe Sperling, Geretsried (DE); Konrad Lex, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 437 days.

(21) Appl. No.: 11/241,827

(22) Filed: Sep. 30, 2005

(65) Prior Publication Data

US 2006/0187453 A1      Aug. 24, 2006

(30) Foreign Application Priority Data

Jan. 26, 2005   (DE) ..................... 10 2005 003 690

(51) Int. Cl.
*G01J 1/44*      (2006.01)
(52) U.S. Cl. ...................................... 356/226; 356/222

(58) Field of Classification Search ......... 356/213–236, 356/73, 402–406, 416–423, 445–448, 600–613, 356/239.1–239.7, 237.2–237.6; 250/559.01
See application file for complete search history.

(56) References Cited

U.S. PATENT DOCUMENTS 5,835,220 A * 11/1998 Kazama et al. ............. 356/369
7,126,681 B1 * 10/2006 Chen et al. ............... 356/237.4

* cited by examiner

*Primary Examiner*—Gregory J Toatley, Jr.
*Assistant Examiner*—Tri T Ton
(74) *Attorney, Agent, or Firm*—Greer, Burns & Crain, Ltd.

(57) ABSTRACT

A device for examining the optical properties of surfaces includes a first radiation source which emits radiation to an examination surface, at least one first detector device, for detecting the radiation reflected off the surface and emitting at least one signal that is characteristic of at least one parameter of the detected radiation, wherein the detector device includes a plurality of image capturing components arranged in a specified detection area and wherein a control is provided for compensating signal changes caused by a shift of the location where the reflected radiation is incident on the detection area.

35 Claims, 2 Drawing Sheets

APPARATUS FOR THE EXAMINATION OF THE PROPERTIES OF OPTICAL SURFACES

FIELD OF THE INVENTION

The present invention relates to a device for examining the optical properties of surfaces. The device will be described below with reference to examining motor vehicle bodies. However, it is contemplated that other kinds of surfaces may also be examined such as the surfaces of furniture and the like.

BACKGROUND

Devices for examining the optical properties of surfaces are known from the prior art. Generally, these devices use a light source which directs light at the examination surface and a detector that detects and evaluates the light reflected or diffused off of the surface. Such evaluation allows a determination of the optical properties of surfaces such as color, gloss, orange peel and the like. Such a determination or characterization is required since motor-vehicle bodies or their paintwork make different impressions on the human eye depending on the incident light, thus requiring a neutral characterization for comparing different surfaces.

The devices known from the prior art are placed on the examination surface. In the prior art there is the problem that for example in the case of curved surfaces, measurement results of identical measuring points also depend on the incident angle of the light on the examination surface. Such curvatures may also lead to incorrect results.

This effect may occur for example when examining paint coatings comprising pigments or so-called flakes. These pigments or flakes are for instance metal particles statistically distributed in the layer of paint or on its surface. The pigments exhibit different characteristics in dependence on the incident angle of the light such as a slightly changed angle of observation, a different color or a different brightness. If present, the reflected light is particularly strongly affected by deviations from the angle of reflection.

SUMMARY

It is therefore the object of the present invention to provide a device for examining the optical properties of surfaces which device allows measurements to be taken also from curved surfaces. All of the embodiments of the present invention are based on the common concept that curved surfaces are taken into account by factoring in the location of incidence of reflected radiation on the detection surface.

The device of the present invention for examining the optical properties of surfaces comprises at least one first radiation means which emits radiation to an examination surface.

At least one first detector detects the radiation reflected off said surface and emits at least one signal that is characteristic of at least one parameter of the detected radiation.

The detector means comprises a plurality of image capturing components arranged in a specified detection area. Furthermore, control means are provided for compensating at least a portion of signal changes caused by a shift of the location where the reflected radiation is incident on the detection area.

Establishing or determining a shift of a location due to a curvature of the surface using radiation incident on the detection surface, does not necessarily have to occur through the first detector means but may also be performed through other means.

Such other means may for example be another detection means which, as does the first detection means, also comprises a plurality of image capturing components so as to allow determining the location where radiation is incident on this further detection means.

Furthermore such other means may be a distance measuring means that determines the distance of selected points of the device relative to the examination surface.

Radiation means is understood to mean any means emitting radiation. Said radiation is preferably a light and particularly preferably light in the visible range. However, use of infrared or ultraviolet light also lies within the scope of the invention.

The output signal is preferably understood to mean an electrical signal that is characteristic of a parameter of detected radiation such as intensity.

Image capturing components are understood to mean elements capable of detecting radiation incident on them and evaluating it applying specified criteria. They are preferably photo cells, photo diodes or the like.

The specified detection area is preferably understood to mean an image capturing surface where the individual image capturing components are for example arranged to form an array.

The entire detection area may be (but not exclusively) configured as a CCD-Chip. This allows a spatially resolved radiation received or imaged on the detection area rather than determination of the total intensity only.

Control means are generally understood to mean such means acting to control processes. Such control means are in particular but not exclusively processors acting on a procedure, and also mechanical controls such as stepping motors or the like.

A shift of the location where the radiation is incident on the detection area is understood to mean that certain radiation portions such as the local radiation portion containing an intensity maximum shifts its position relative to the detection area, i.e. the incidence on the detection area is offset or displaced.

This shift of the location or more precisely the change of the output signal caused by this shift of the location, is at least partially compensated as the signal is evaluated or output i.e. the control means preferably act such that a shift of the location of incidence of radiation in the detection area will cause substantially no change of the output signal.

It is conceivable though, without departing from the solution of the invention, that the output signal varies in relation to the location of incidence of the radiation in the detection area while at the same time correction parameters are output so as to allow a compensation for the shifting location. Such correction parameters allow a user to simultaneously draw conclusions on the characteristics of the curvature itself.

A preferred embodiment provides a detection area having a plurality of subareas outputting at least partially predefined signal portions wherein the control means act to cause that predefined subareas of the detection area are factored in for signal output in different ways, at least intermittently.

A subarea of the detection areas is understood to mean a portion of the detection area, for example a surface portion of the detection area containing a predefined portion of the total number of image capturing components. An individual image capturing component may also be understood to be a subarea.

Both the detection areas and the subareas may have any arbitrary geometrical shape such as a square shape, rectangular shape, circular shape, ellipsoid shape and the like.

Factoring in in different ways is preferably understood to mean that a specified subarea of the total detection area will be weighted specifically or to a greater extent when evaluating the received radiation.

In the case of a substantially flat examination surface the returning and in particular the reflected or diffused light is projected or imaged onto a specified area of the detector means or the detection area. This may for example be a center subarea of the detection area. However, if the examination surface is curved and thus the measuring instrument may be tilted relative to the surface. The returning light, and in particular, the reflected or diffused light is imaged onto a different subarea of the detection area, for example onto an area that is displaced relative to the center area. In such a case the device of the invention causes the usual central subarea of the detection area instead of a subarea that is displaced from the detection area to be evaluated.

Another preferred embodiment provides that the signal portion output from a first predefined subarea is associated with another predefined subarea at least intermittently.

It should be taken into account that the signal portion output from the predefined subarea correlates with this portion of radiation imaged on this subarea. If a curvature of the examination surface causes this radiation portion to be imaged onto another subarea of the radiation surface, the signal portion that is now output from the further subarea is associated with the first predefined subarea. It is also conceivable that the signal portion output from individual image capturing components is associated with different image capturing components. This way allows an evaluation of the radiation imaged onto the entire detection area while also factoring in that the location of incidence of the radiation in the detection area has changed due to a curvature in the examination surface.

In a preferred embodiment the control means act such that in outputting the signal or when factoring in a shift in location, that subarea of the detection area will be weighted to a greater extent or exclusively where the highest intensity radiation is incident. This means that those image capturing components of the detector means are selected where the highest intensity radiation is incident and the subarea which is weighted to a greater extent in outputting the signal, will be selected such that said image capturing components are included in said subarea. In this way it is possible to select that subarea where the radiation deflected by a curvature or the portion of the highest intensity radiation is projected.

In another preferred embodiment one of a number of radiation means is arranged substantially at the angle of reflection relative to the test piece and the detector means wherein for compensating the shift in location where the reflected radiation is incident on the detection area, said radiation originating from said radiation means is substantially taken into account. The angle of reflection is understood to mean that the radiation means, the surface and the detector means are positioned relative to one another such that the light emitting from the radiation means and reflected from the test piece reaches the detector surface. Additionally the mentioned detector means is preferably employed for determining gloss or distinctness of image.

This configuration achieves that the light examined in regard of compensation of changes will primarily be the strongest emitting from or reflected off the surface in the direction of the detector means since evaluation of this light is easier than evaluation of light diffused in other directions as regards intensity. More precisely this configuration means that the light emitting from the selected radiation means is detected by the detector means at the angle of reflection.

In another preferred embodiment the signal change caused by a shift of the location where the reflected radiation is incident on the detection area, is determined by means of at least one length measuring means wherein said length measuring means determines the distance of at least one device component relative to the surface. It is preferred that predefined locations on the device, which are particularly preferably arranged adjacent to the surface, have a number of length or distance sensors located at them which determine the exact position of the device relative to the examination surface and in this way allow compensation of the output signal.

A compensation of changes of the output signal is preferably performed by determining the change of the enclosed angle between the radiation incident on the surface and the radiation reflected back from the surface. This angle or the change of this angle is determined for compensation and more information about the examination surface is preferably furnished. This angle can also be used for compensation of interference effects.

Another embodiment also provides for another radiation means to be arranged such that the light emitting from it and diffused off the surface is captured by the detector means.

Another preferred embodiment provides a plurality of further detector means which detect the radiation reflected back from the surface and which output a signal characteristic of at least one parameter of said radiation. Particularly preferably at least one of said further detector means comprises a plurality of image capturing components located in a specified detection area. In this embodiment one of said further detector means serves to determine a shift of the location where the radiation is incident. This shift of the location or change of the signal caused by this shift of the location is factored in and/or compensated at least in the first detector means, preferably also in further detector means.

In a preferred embodiment another detector means is located at the angle of reflection in relation to the incident radiation and serves to determine a shift of the location where the radiation is incident and thus to determine the changes caused by a curvature of the surface. These changes determined will then be factored for with compensation of the output signal from the first detector means. These changes can preferably also be used for output signals of further detector means.

It is preferred that the detector means comprising a plurality of image capturing components are arranged near the angle of reflection relative to the incident light, i.e. in the range of 90°, preferably 45° and very preferably 25° around said angle. Other detection means arranged outside this angular range preferably comprise no image capturing components, thus only allowing a determination of the total intensity of radiation received.

Another preferred embodiment provides adjusting means for shifting the location of radiation incidence on the detection area.

An adjusting means is understood to mean such means capable of shifting the position of an object relative to another object. These may for example be motor-driven adjusting screws or the like.

Preferably the adjusting means cause the detection area to move relative to the device.

Another preferred embodiment provides that the adjusting means cause the entire device to move relative to the examination surface.

This embodiment according to the invention solves the object of the invention to compensate beam deviations caused by curved surfaces, as does the above described embodiment.

While the above embodiment provides that the evaluation area of the detector means is adjusted electronically or by means of software, this case provides that the position of the detection area is changed relative to the incident radiation and in this way the detector means is set such that the radiation will return to be received in the subarea provided initially which is for example a central subarea.

It is also conceivable to combine the variant described above with this described variant i.e. to perform corrections both electronically by electronically adjusting the subarea, and on the other hand by a movement of the detection area relative to the incident radiation. This may in particular but not exclusively be preferred where due to the surface curvature the reflected beams are deflected to such an extent that they are not completely incident in the detection area.

Another embodiment provides that measuring results from too greatly curved surfaces are recognized and discarded. This may for example occur when an intensity maximum of the radiation moves out of the detection area during measuring when the device is moved relative to the surface.

In a preferred embodiment the adjusting means are controlled by a processor unit, such that in relation to the position of the radiation imaged on the detector means, they specify in a predetermined way, the position of the device relative to the examination surface. This means that, if the radiation imaged on the detection area is deflected by a specified range of length, the detection area is displaced relative to the radiation by just this range of length or distance.

Preferably said adjusting means cause the detection area to move relative to the radiation such that the reflected radiation is incident in a predefined subarea of the detection area. It is particularly preferred that this is the subarea of the detection area where the radiation would be incident in the case of an non-curved surface.

Another preferred embodiment provides, in the optical path between the radiation means and the detector means, an imaging component that is imaged onto the detection area. Optical means such as lenses and the like may be employed for imaging said imaging component.

The imaging component is preferably a punctiform body. In another preferred embodiment the imaging component is a diaphragm.

Imaging the imaging component onto the detector means results in a shadow and thus an intensity minimum to be generated at the location where imaging occurs. In many applications, making adjustments by an intensity minimum is easier than by an intensity maximum. Therefore any adjustments or readjustments required can be made by the imaging component imaged on the detection area. The location onto which the imaging component is imaged can also be employed for factoring in or possibly discarding, measuring results taken from too greatly curved surface portions.

Other preferred embodiments provide control means which cause that the location at which the radiation is incident on the detection area is shifted in relation to the location on the detection area where the imaging component is imaged.

The location where the imaging component is imaged on the detection area, takes a defined and substantially constant position relative to the entire imaged radiation on the detection area. As mentioned above, in this way any adjustments can be made by the location where the imaging component is imaged. During this, both electronic selection of the subarea by means of the imaging component and mechanical readjustment of the detection area relative to the incident radiation may be performed.

Another preferred embodiment provides a plurality of radiation means. These radiation means are preferably arranged at specified angles relative to the surface wherein it is particularly preferred that the individual angles differ from one another. The different radiation means serve to let the light be incident onto the surface at different angles and to subsequently have the detector means detect the returning light reflected off said surface.

A plurality of detector means may be provided which detect light at different angles. The radiation means may comprise any desired light sources such as in particular but not exclusively halogen lamps, light-emitting diodes of different wavelength ranges and the like. Further detector means may also be provided which do not allow of detection radiation.

Another preferred embodiment provides that the imaging component is located in an optical path between the radiation means and the examination surface. In this way a change in the beam direction caused by a curved surface will substantially influence in the same way both a shift in the location where the imaging component is imaged and in the location where the radiation is incident on the detector means.

In another preferred embodiment the imaging component is arranged at a selected radiation means and particularly preferably at that radiation means the light from which is incident at a predefined angle such that the light emitting from said radiation means is detected by the detector means substantially at the angle of reflection.

As mentioned above, the light incident and detected at the angle of reflection is suitable for adjusting or electronically changing the respective subareas since the most intensive light can be employed for determining such changes.

Another preferred embodiment provides a processor assembly which determines the position of the device relative to the examination surface from the location on the detector means where the imaging component is imaged. More precisely, the location where the imaging component is imaged serves to determine the respective local curvature of the surface or the tilt of the device relative to the surface. When the device is moved relative to the examination surface the surface outline of the examination surface or the shape of the curve can be determined in this way.

Another preferred embodiment provides a processor assembly which compensates the output signal by figuring in the location on the detector means where the imaging component is imaged. This means that it is determined at which location on the detector means or at which location in the detection area the imaging component is imaged. This location is compared with a starting location (when measuring a flat surface) and factoring in this deviation, adjusts or compensates the output signal from the detector means, preferably by determining the offset of the radiation caused by the curvature.

For this purpose a storage device is preferably provided where a functional connection is stored that allows a correction of the output signal from the location on the detector means where the imaging component is imaged.

The above modi of operation are also conceivable without using the imaging component for example by making adjustments also at the location where an intensity maximum occurs.

Another preferred embodiment provides for adjusting the use of another radiation means which emits substantially convergent radiation such as a laser whose light reflects in the direction of the detection area. Due to a curved surface, the laser point also imaged on the detection area is displaced, based on these deflections the above mentioned corrections of the output signal can be determined.

Another preferred embodiment provides that the adjusting means changes an angle relative to the examination surface. This means that the entire device is moved relative to the examination surface and in this way the angle at which the light is incident on and reflected off the examination surface is corrected.

The present invention further relates to a method for examining the optical properties of surfaces where in a first process step, a radiation is emitted onto an examination surface by means of a first radiation means at a specified angle. In another process step the radiation reflected off the surface is detected by means of a first detector means wherein the detector means comprises a plurality of image capturing components located in a specified detection area.

In another process step a signal is output which is characteristic of at least one radiation parameter wherein a shift of the location where the reflected radiation is incident on the detection area, is compensated.

In another process step a subarea of the detection area is preferably determined where a selected portion of the radiation is incident and the determined subarea is factored in in a specified way.

Preferably the signal portion output from a predefined subarea is associated with another predefined subarea at least intermittently.

The selected portion of the radiation is preferably that portion having the highest radiation intensity. Preferably the determined subarea is weighted more for compensation of the shift of the location where the reflected radiation is incident on the detection area.

The method according to the invention also solves the object on which the invention is based, to correct deflections caused by unevenness of the examination surface.

These deflections cause the beam reflected off the surface to be incident at another location in the detection area than in the case of a flat surface. Based on this deflection the corresponding subarea of the detection area is determined and preferably in such a way as to select the location where the highest intensity radiation portions occur.

Another method of the invention provides that an imaging element located in the optical path between at least one radiation means and the detector means is imaged onto the detection area. In this case a subarea is preferably determined by the intensity minimum caused by the image.

The compensation of the shift of the location on the detection area caused by the curvature of the surface is preferably achieved by determining the location at which the imaging component is imaged.

Preferably the position of the detection area is changed relative to the reflected radiation.

This method of the invention also serves for correcting deflections caused by curved surfaces. Instead of an electronical correction any corrections in this case are made by readjusting the detector means or the respective detection area.

The methods of the invention presented above may be combined by performing both an electronic correction by determining a subarea and a mechanical correction by readjusting the detection area.

Any change of position of the detection area is preferably performed in relation to the position of the radiation imaged onto the detection area. Other advantages and embodiments of the present invention can be taken from the accompanying drawings.

DETAILED DESCRIPTION

Figure 1:
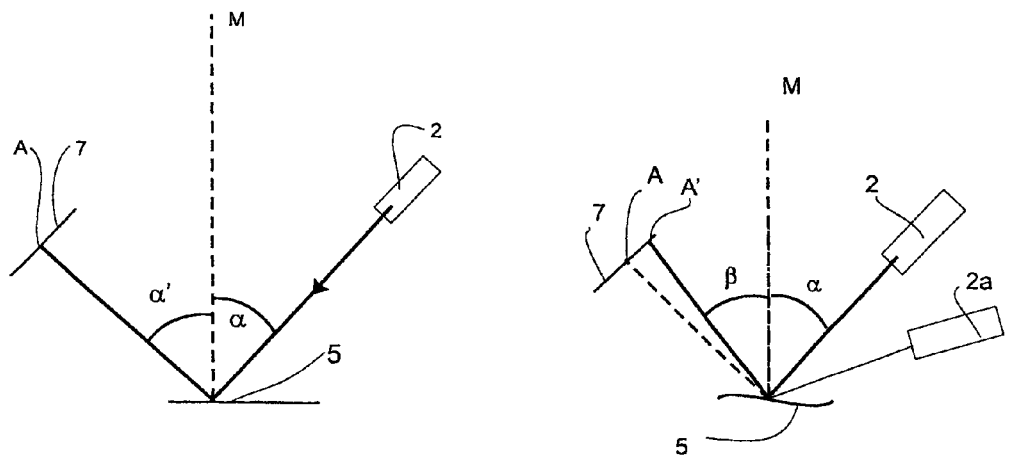
FIG. 1 is a schematic representation for illustrating the object on which the invention is based.

FIG. 1 is a schematic representation for illustrating the object on which the invention is based. Radiation emits from a radiation means 2 onto an examination surface 5. The radiation returning from, in the case of FIG. 1 reflected off, this surface passes onto the detection area 7 of a (not shown) detector means where it is incident in the area A. When the examination surface 5 is without curves, i.e. flat, the light will be reflected such that the angle $\alpha$ equals the angle $\alpha'$ relative to the perpendicular bisector M. If, however, as shown in the second subfigure of FIG. 1, the surface is curved, the angle relative to the perpendicular bisector M at which light is reflected off the surface takes a value $\beta$ that is different from $\alpha$, in relation to the degree of curvature of the surface 5. Thus the location at which the reflected radiation is incident in the detection area 7 (point A'), differs from the location at which it would be incident if the surface were flat (point A). If this offset were not factored in or compensated, the measuring result would be incorrect. Or more precisely, measuring results supplied from other detection means positioned at other angles of reflection than shown herein, would then also be incorrect.

Reference numeral 2a indicates another radiation means emitting light to the surface 5. Herein, light diffused off the surface 5 is projected onto the detection area 7. In this case it may happen that surface unevenness would change the color impressions of the examination surface and at different positions i.e. in different image capturing components or subareas, the detection area 7 would receive different color impressions than if the surface were flat. The present invention therefore proposes to shift the areas to be evaluated or to allocate to different subareas, information received or output from specified subareas, wherein deflection of the radiation is factored in with such allocation.

In this way it is possible to receive the same color impression that would be received if the surface were flat at the area of examination or if the device were not tilted. This explanation relates to a case where multiple radiation means are employed. A corresponding application is also conceivable in embodiments comprising one radiation means and multiple detector means, as will be described below.

Figure 2:
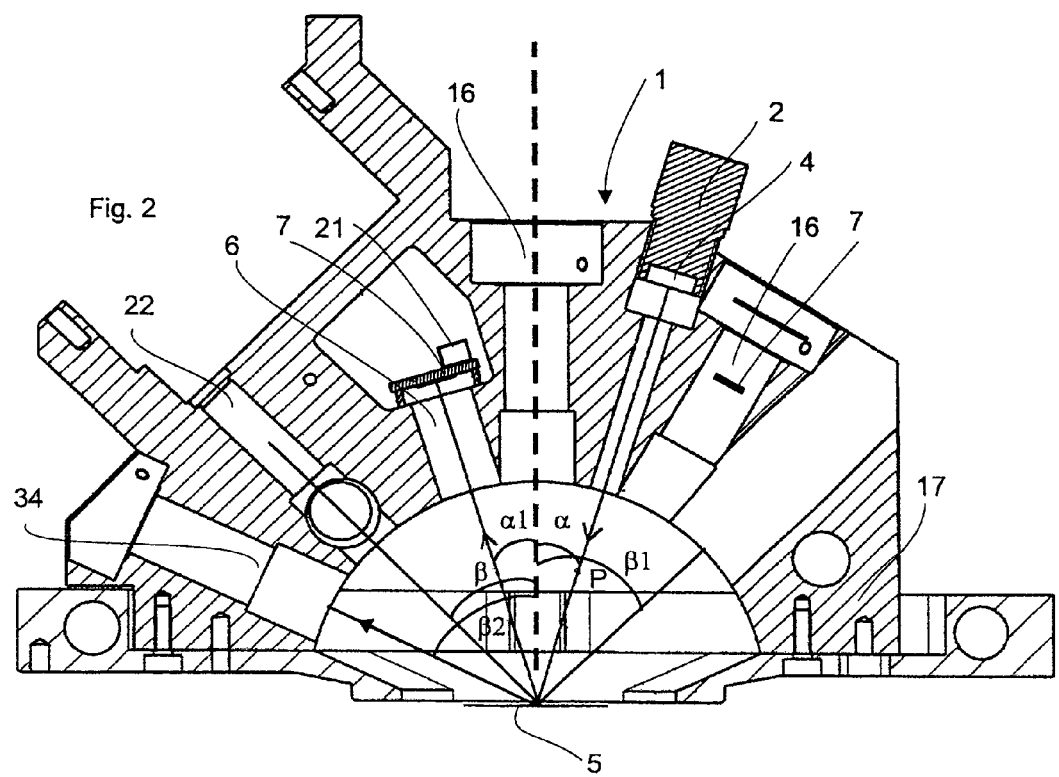
FIG. 2 is a device of the invention for examining the optical properties of surfaces.

FIG. 2 shows the device of the invention for examining the properties of surfaces. It comprises a radiation means 2 which directs radiation along the arrow P at an angle $\alpha$ relative to the perpendicular bisector 11 onto the examination surface 5. The radiation means comprises a radiation source 4 which is in particular but not exclusively a radiation source selected from a group of radiation sources including halogen lamps, mercury vapor lamps, normal light bulbs, light-emitting diodes and the like. Radiation means may also be understood to mean a plurality of light-emitting diodes in particular but not exclusively at different emission ranges.

Reference numeral 6 refers to another detector means in this case located at the angle of reflection, reference numeral 7 to a detection area. This detection area has a plurality of image capturing components (not shown in FIG. 2) located in it.

Apart from detector means 6, first detector means 16 are provided. The light incident on these detector means is also evaluated. The further detector means 16 similar to the detector means 6 also comprise image capturing components (not shown) which are located in detection areas 7 so as to allow a spatially resolved presentation of incident radiation. As mentioned initially, the properties of such light or such radiation are very sensitive to the angle of incidence of the light on the surface 5.

In the embodiment shown in FIG. 2 the detector means 6 is used to determine a shift of the location where the radiation is incident. This shift is factored in for the output signal of the detector means 16 in that, as initially described and as will be described below in more detail, the subareas are adjusted. In this case radiation originates from, preferably at least including, the radiation means 22.

Reference numeral 34 indicates another detector means. Since this detector means is located at an angle that is far distant from the angle of reflection $\beta 2$, it does not comprise a plurality of image capturing components, thus only allowing a determination of the intensity of incident radiation without spatial resolution. Reference numeral $\beta$ indicates the angle of incidence on the surface 5 of the light emitting from the radiation means 22 and the reference numeral $\beta 1$, the angle of reflection at which the light emitting from the radiation means 22 is reflected.

Reference is made to the fact that the illustrated compensation of the output signals is relevant in particular near the angle of reflection since the effects of changes caused by curvatures of the surface will naturally be particularly serious there. For example with light incident on so-called flakes the variations in the color impression may be particularly extreme in just these angular ranges. This is the reason why the detector means employed are preferably such means which allow also color resolution.

Reference numeral 17 refers to an optic unit where the individual radiation means and detector means are located. An adjusting means 21 is employed in one embodiment to vary the position of the detection area 7 relative to the incident radiation, indicated by arrow P.

The device further comprises a processor assembly (not shown) for controlling the detection area 7 and in particular for selecting the subareas or shifting the detection area relative to the incident radiation.

Another embodiment provides adjusting means (not shown) for changing the position of the entire device 1 relative to the surface 5 and in this way effecting a correction of deflections caused by curved surfaces. In detail, the device will in this case be set such that the perpendicular bisector M of the device is positioned substantially perpendicular to the examination portion of the surface 5.

Figure 3A:
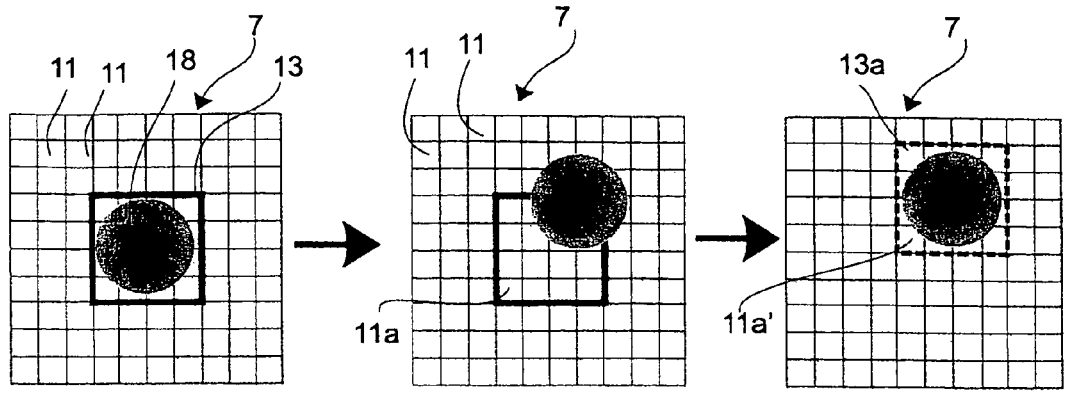
FIG. 3a is a schematic representation illustrating the method of the invention.

FIG. 3a shows a first method of the invention for correcting deflections. The left subpicture in FIG. 3a shows detection area 7 which comprises a plurality of image components 11 arranged in an array that in this case is quadratic. It is also conceivable to choose other shapes for the detection area 7 such as generally rectangular areas, circular areas and the like. In the case of a flat surface the radiation returning from or reflected off the surface is incident on the subarea 13 indicated by the black square. In a preferred embodiment this is a central area of the detection area 7.

The radiation point 18 is an idealized circular illustration. The radiation point 18 preferably originates from the radiation means which is located at the angle of reflection relative to the detector means or the detection area. In FIG. 3a the incident radiation has its maximum intensity in the center of the radiation point. The center subpicture in FIG. 3a shows the situation where a curved surface causes the beam 18 to be no longer incident in the subarea 13 but shifted to the side and upwardly thereof. In reality the radiation point will not be homogeneous nor will it have the circular shape shown herein. Preferably a corresponding diaphragm arrangement causes the point to take a substantially rectangular or standardized shape.

The situation in respect of the further radiation means or detector means will have the effect that light emitting from these radiation means is diffused into different spectral portions or light incident on the further detector means will be received at different spectral portions. The picture on the right in FIG. 3a has the area 13 shifted such that the radiation point 18 is substantially back again inside this subarea. This means that the image capturing components relevant for the radiation point 18 will only remain those image capturing components located within the shifted subarea 13a. This shifting allows to determine the deviation caused by the curved surface of the location of incidence of the beam on the detection area.

The shifting of the radiation point for example causes the image capturing component 11a shown in the center subpicture to receive the same information as does the image capturing component 11a' shown in the subpicture on the right. Selecting the different subareas 13a and 13a' will thus allow that, shifting of the radiation point 13 due to the curvature notwithstanding, the same information will be obtained as in the subpicture on the left in FIG. 3a and thus the shift caused by the curvature will be compensated.

This deviation of the radiation location determined in the detection area can be transmitted to the detection areas in other detector means, i.e. the corresponding subareas in the other detector means can also be adjusted. The signals from other detector means will also be compensated in this way. This means that a detector means, preferably the one located at the angle of reflection, will determine the geometrical shift of the point of incidence of the radiation wherein said shift will correspondingly be applied to at least some of the other detector means. The reason therefor is, as explained above, that this shift of the location will have effects in particular on the other detector means such as color changes and therefore a correction is preferred in particular also in the other detector means.

Figure 3B:
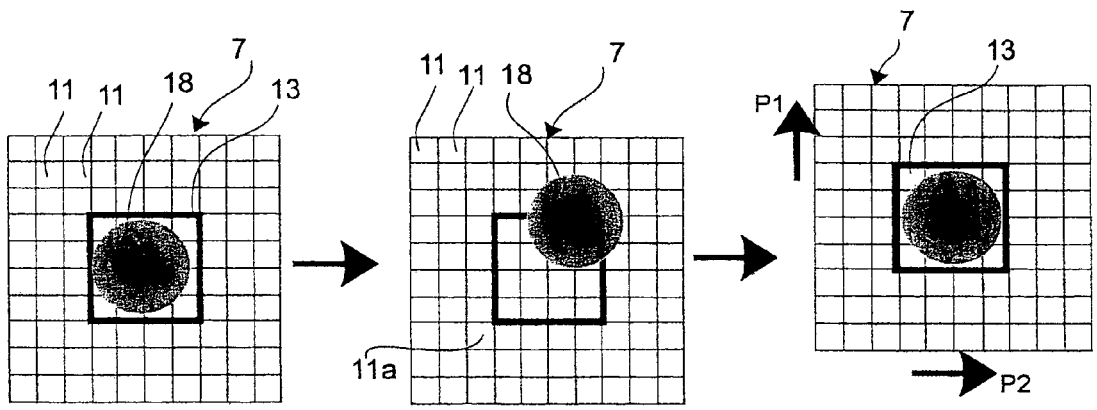
FIG. 3b is a schematic representation illustrating the method of the invention.

FIG. 3b shows another method of the invention which serves to compensate for the shifting of the radiation point 18 caused by curved surfaces. The subpicture on the left again shows the normal situation where measurement is taken from a substantially flat surface. In the center subpicture, as in the center subpicture of 3a, the radiation point 18 moves to a position offset relative to the initial position. In the subpicture on the right the entire detection area 7 is moved along the arrows p1 and p2 to the right and upwardly such that the radiation point 18 is substantially back again inside the subarea 13. In this case all of the image capturing components 11 will receive substantially the same information both in the subpicture in the middle and on the right, since the detection area is shifted as a whole.

Figure 3C:
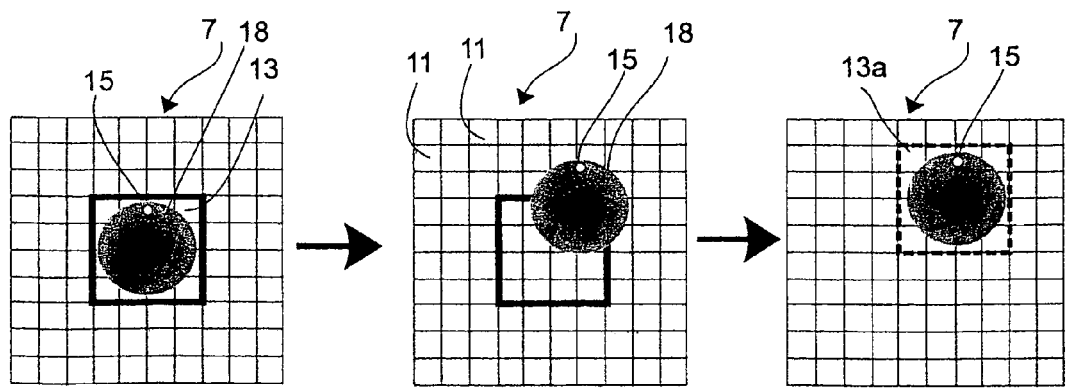
FIG. 3c is a schematic representation illustrating the method of the invention.

FIG. 3c shows another embodiment of the method of the present invention. In this case, reference numeral 15 refers to an image of an imaging component on the detection area 7. As mentioned initially, making adjustments or calibrating by an intensity minimum is easier in many applications than by an intensity maximum. Still, when the imaging component is positioned in the optical path between the radiation means 2 shown in FIG. 2 and the detector means 5, there will always be a precisely defined relation between the imaging point 15 and the radiation point 18 such that adjustment or compensation can be made by this minimum. The spatial relation between the imaging point 15 and the radiation portions from the other radiation means 16 (FIG. 2) diffused at the test piece is also specified and substantially does not vary. The method shown in FIG. 3*c* resorts to the principle of the method shown in FIG. 3*a*. It is, however, also conceivable to employ the method shown in FIG. 3*b* using the imaging component or the imaging point 15.

The shifting shown in FIG. 3*b* of the detection area can be achieved by moving only the detection area itself; however it is conceivable to move the entire detector means or to change the position of the entire device 1 shown in FIG. 2 relative to the surface 5.

The embodiments shown in FIGS. 3*b* and 3*c* can be modified in the above way by transmitting to other detector means, a shifting of the location determined on one detector means.

The invention claimed is:

1. A device for examining the optical properties of surfaces comprising:
    a first radiation means which emits radiation to an examination surface;
    at least one first detector means, for detecting the radiation reflected off said surface and emitting at least one signal that is characteristic of at least one parameter of the detected radiation, said first detector means including a plurality of image capturing components arranged in a specified detection area; and
    control means for compensating at least a portion of signal changes caused by a shift of the location where the reflected radiation is incident on said detection area, said control means acting such that a shift of the location of incidence of the radiation in the detection area causes substantially no change of said signal.

2. The device according to claim 1, wherein said detection area has a plurality of subareas which output at least partially predefined signal portions of said signal and that said control means acts to cause said subareas of said detection area to be factored in in different ways, at least intermittently.

3. The device according to claim 2, wherein said predefined signal portion outputted by one of said subareas is associated with another one of said predefined subareas, at least intermittently.

4. The device according to claim 2, wherein said control means causes at least one of said subareas of said detection area to be weighted higher for signal output.

5. The device according to claim 2, wherein said control means causes at least one of said subareas of said detection area is weighted higher for signal output where said radiation at the highest intensity is incident.

6. The device according to claim 2, wherein said at least one first radiation means is located substantially at an angle of reflection relative to a test piece and said at least one first detector means wherein for compensating the shift in location where the reflected radiation is incident on the detection area, radiation originating from said radiation means is substantially taken into account.

7. The device according to claim 1, wherein a shift of the location where the reflected radiation is incident on the detection area, is determined by means of at least one length measuring means wherein said length measuring means determines a distance of at least one selected device component relative to said examination surface.

8. The device according to claim 1, wherein a plurality of further detector means are provided which detect the radiation reflected off said surface and which output a signal characteristic of at least one parameter of said radiation.

9. The device according to claim 8, wherein said at least one of said plurality of further detector means comprises a plurality of image capturing components located in a specified detection area.

10. The device according to claim 1, further comprising adjusting means for shifting the location of incident radiation in said detection area.

11. The device according to claim 10, wherein said adjusting means allows said detection area to move relative to the device.

12. The device according to claim 10, wherein said adjusting means allows said device to move relative to said examination surface.

13. The device according to claim 10, wherein said adjusting means is controlled by a processor assembly such that in dependence on the position of the radiation imaged on said first detector means, a position of the device relative to said examination surface is determined in a specified way.

14. The device according to claim 10, wherein said adjusting means allows movement of said detection area relative to the reflected radiation such that the reflected radiation is incident on a predetermined subarea of said detection area.

15. The device according to claim 1, wherein one of said image capturing components in said detection area is positioned in an optical path between said first radiation means and said first detector means.

16. The device according to claim 15, wherein said imaging capturing component is a punctiform body.

17. The device according to claim 15, wherein said imaging capturing component is a diaphragm.

18. The device according to claim 1, wherein said control means causes the location at which the radiation is incident on said detection area to be shifted in consideration of the location on said detection area where at least one of said imaging capturing components is imaged.

19. The device according to claim 1, further comprising a plurality of said first radiation means.

20. The device according to claim 1, wherein each of said first radiation means is arranged at a specified angle relative to said examination surface, wherein each of said specified angles are different from one another.

21. The device according to claim 15, wherein said imaging capturing component is arranged in an optical path between said first radiation means and said examination surface.

22. The device according to claim 15, wherein said imaging capturing component is arranged at a selected one of said first radiation means.

23. The device according to claim 22, wherein light emitted by said first radiation means is incident at a specified angle such that said light is detected by said first detector means substantially at the angle of reflection.

24. The device according to claim 1, further comprising a processor assembly which determines a position of the device relative to said examination surface from the location on said first detector means of one of said image capturing components.

25. The device according to claim 1, further comprising a storage device wherein a functional connection is stored on said storage device that allows a correction of said at least one signal from the location on said first detector means of one of said image capturing components.

26. The device according to claim 10, wherein said adjusting means adjusts at least one angle relative to said examination surface.

27. A method for examining the properties of optical surfaces including the method steps:
   emitting radiation by at least one first radiation means at a predetermined angle to an examination surface;
   detecting the radiation reflected off said examination surface by a first detector means, wherein said first detector means comprises a plurality of image capturing components arranged in a specified detection area; and
   outputting a signal, which is characteristic of at least one radiation parameter, wherein a change of said signal caused by a shift of the location on which the reflected radiation is incident on said detection area, is compensated at least in part, and wherein the shift of the location of incidence of the radiation in said detection area causes substantially no change in said signal.

28. The method according to claim 27, wherein a subarea of said detection area is determined where a selected portion of the radiation is incident on said determined subarea and said determined subarea is factored in in a specified way.

29. The method according to claim 28, wherein a signal portion outputted by a predefined subarea is associated with the location of another predefined subarea, at least intermittently.

30. The method according to claim 28, wherein said selected portion of the radiation is the portion having the highest radiation intensity.

31. The method according to claim 28, wherein said determined subarea is weighted higher for compensation of the shift of the location where the reflected radiation is incident on said detection area.

32. The method according to claim 27, wherein at least one image capturing component is arranged in an optical path between said at least one first radiation means and said detector means.

33. The method according to claim 32, wherein said subarea of said detection area is determined from the location at which said imaging component is imaged on said detection area.

34. The method according to claim 27, wherein a position of said detection area is changed relative to the reflected radiation.

35. The method according to claim 27, wherein a position of said detection area is changed relative to the position of the radiation imaged on said first detector means.

* * * * *